(12) United States Patent
Sheth et al.

(10) Patent No.: US 10,405,551 B2
(45) Date of Patent: Sep. 10, 2019

(54) MANAGING ETHYLENE IN PLANTS USING A SYNERGISTIC AGRICULTURAL FORMULA COMPRISING DIACYL OR DIARYL UREA AND AT LEAST ONE METAL COMPLEX

(71) Applicant: Stoller Enterprises, Inc., Houston, TX (US)

(72) Inventors: Ritesh Sheth, Friendswood, TX (US); Jerry Stoller, Houston, TX (US); Robert R. Shortell, Houston, TX (US)

(73) Assignee: Stoller Enterprises, Inc., Houston, TX (US)

( * ) Notice: Subject to any disclaimer, the term of this patent is extended or adjusted under 35 U.S.C. 154(b) by 0 days.

(21) Appl. No.: 15/288,849

(22) Filed: Oct. 7, 2016

(65) Prior Publication Data

US 2017/0099841 A1    Apr. 13, 2017

Related U.S. Application Data

(60) Provisional application No. 62/238,169, filed on Oct. 7, 2015.

(51) Int. Cl.
*A01N 47/34* (2006.01)
*A01N 59/16* (2006.01)
*A01N 47/30* (2006.01)

(52) U.S. Cl.
CPC ............. *A01N 47/34* (2013.01); *A01N 47/30* (2013.01)

(58) Field of Classification Search
CPC ......... A01N 59/16; A01N 47/28; A01N 59/14
See application file for complete search history.

(56) References Cited

U.S. PATENT DOCUMENTS

| | | |
|---|---|---|
| 5,997,600 A | 12/1999 | Dean |
| 6,040,273 A | 3/2000 | Dean |
| 8,207,091 B2 | 6/2012 | Stoller et al. |
| 2013/0116119 A1* | 5/2013 | Rees ............ A01N 37/10 504/103 |
| 2015/0150261 A1 | 6/2015 | Liptay et al. |

FOREIGN PATENT DOCUMENTS

| | | |
|---|---|---|
| DE | 2552867 A1 | 6/1977 |
| GB | 2522065 A | 7/2015 |
| WO | 2016007941 A1 | 1/2016 |

OTHER PUBLICATIONS

CN 104109021 A in machine translation (2017).*

* cited by examiner

*Primary Examiner* — Alton N Pryor
(74) *Attorney, Agent, or Firm* — Yancy IP Law, PLLC

(57) ABSTRACT

A synergistic agricultural formula including at least one diacyl or diaryl urea, such as a N,N'-diformylurea, and at least metal complex, such as metal complexes of cobalt, nickel, silver or other metals, is applied to plants at physiologically sensitive times resulting in prolonged and complete ethylene reduction. This synergistic agricultural formula gives those skilled in the art the ability to regulate important phenotypical parameters that lead to a variety of important agronomic and horticulture traits which improve crop yield parameters leading beyond that of its individual components.

16 Claims, 1 Drawing Sheet

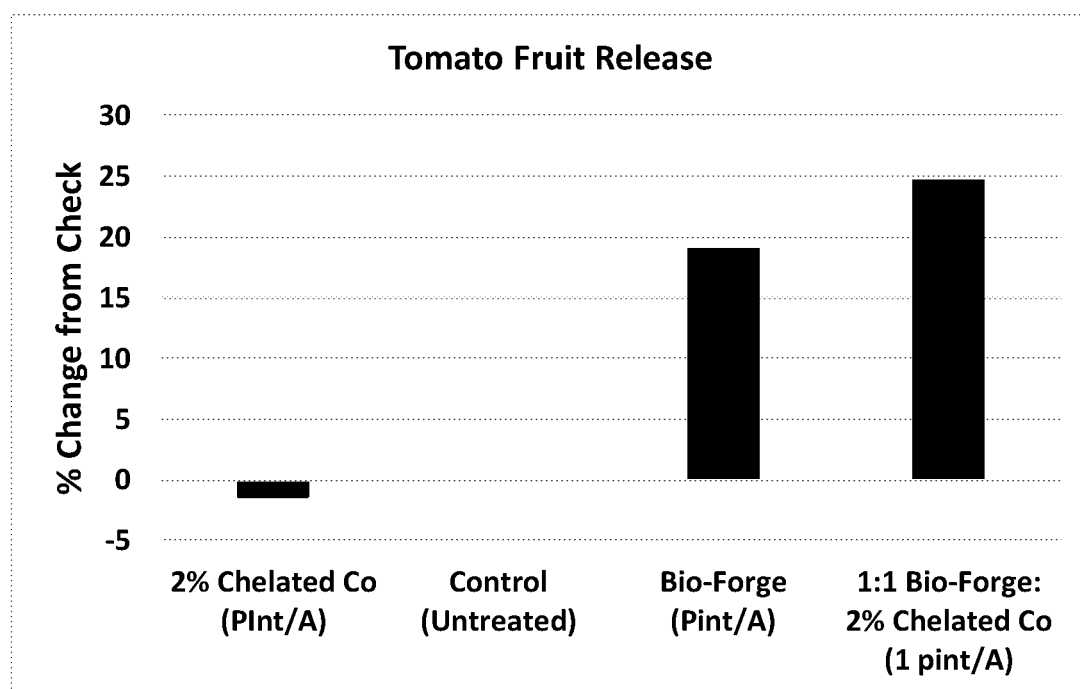

MANAGING ETHYLENE IN PLANTS USING A SYNERGISTIC AGRICULTURAL FORMULA COMPRISING DIACYL OR DIARYL UREA AND AT LEAST ONE METAL COMPLEX

CROSS-REFERENCE TO RELATED APPLICATION

This Application claims the benefit, under 35 U.S.C. 119(e), of U.S. Provisional Patent Application No. 62/238,169 filed Oct. 7, 2015, the contents of which are incorporated herein by reference.

BACKGROUND OF THE INVENTION

1. Field of the Invention

The present invention generally relates to a synergistic agricultural formula including at least one diacyl or diaryl urea and at least one metal-complex.

2. Description of the Background

Ethylene is a gaseous hydrocarbon used in a wide range of industrial and agricultural applications. It is produced naturally in plant cells and regulates the cell cycle and natural ripening and aging process in plants. In agriculture, ethylene concentration is often manipulated using exogenous applications of ethylene, ethylene precursors and promoters and ethylene inhibitors to control cell cycling, the crop's response to the environment, flowering, fruit retention and ripening.

Ethylene levels also increase in plants as a direct response to environmental stress through the signaling pathway of reactive oxygen species. Wherein inefficient use of the suns energy through the plants photosynthetic apparatus cause the buildup of reactive oxygen species, which then signal the conversion of 1-aminocyclopropane-1-carboxylic acid (ACC) into cellular ethylene. This buildup of ethylene offsets the plants hormone balance and leads to premature crop decline.

Chemical applications are widely used in agriculture to inhibit ethylene in plants. Through these practices those skilled in the art of the science can achieve a variety of agronomic and horticultural advantages in their cropping systems. These effects would include, but are not limited to, increased fruit retention, improvements in root architecture and reductions in environmental stress responses that can ultimately promote juvenility, growth and other yield parameters resulting in increased yield. Effective chemical applications are often limited by application timing, crop type, economics and regulatory actions in the specific regions the applications are warranted.

Adequate inhibition of ethylene can be used throughout the crops lifecycle to promote juvenility and improve root architecture, by promoting hormone balance and natural apical dominance within the plant. Inhibition during flowering and fruit sizing can increase flower and fruit set, fruit size and fruit retention. Inhibition after fruit sizing can delay ripening and extend the cropping system. Ethylene inhibition during stressful environmental events can reduce the effects of stress promoting normal growth and development and decreasing plant damage from said stress.

Elemental cobalt and solutions thereof are well known to reduce ethylene levels in plants. Cobalt works by actively blocking the conversion of ACC into ethylene. This has the added benefits of increasing the ACC pool, leading to the increased production of beneficial polyamines within the plant cell. However, cobalt applications are only partially effective in blocking this pathway, therefore cellular physiological phases and or environmental factors can overwhelm this mechanism resulting in incomplete ethylene inhibition and ultimately a disruption in the hormone balance, leading to decreased product and application efficacy.

N,N'-diformylurea is a proprietary organic molecule that also inhibits ethylene production in plants. It functions by quenching the reactive oxygen species signal that causes the conversion of ACC to ethylene. This molecule shows dramatic effects in inhibiting excess cellular ethylene resulting in the maintenance of hormonal balance, plant growth and productivity. However, under conditions that favor ethylene production; N,N'-diformylurea is limited by its intracellular concentration. Excesses of reactive oxygen species can overwhelm the reactive oxygen species scavenging ability of the N,N'-diformylurea and allow ethylene signals to leak through, thus reducing its efficacy. This effect is reduced by using multiple exogenous applications over a seven to fourteen day intervals throughout the duration of excess reactive oxygen generation; but this use pattern is only economically feasible in very specific situations where crop value exceeds the cost of application over time. This limits its value in some agricultural situations.

SUMMARY OF THE INVENTION

A synergistic agricultural formula including at least one diacyl or diaryl urea, such as a N,N'-diformylurea, and at least metal complex, such as metal complexes of cobalt, nickel, silver or other metals, is applied to plants at physiologically sensitive times providing a synergistic interaction of the base components resulting in prolonged and complete ethylene reduction. This synergistic agricultural formula gives those skilled in the art the ability to regulate important phenotypical parameters that lead to a variety of important agronomic and horticulture traits which improve crop yield parameters leading beyond that of its individual components.

BRIEF DESCRIPTION OF THE DRAWINGS

The features and advantages of the present invention will become apparent from the following detailed description of a preferred embodiment thereof, taken in conjunction with the accompanying drawings, in which:

FIG. 1 is a graph showing the results a synergistic agricultural formula in accordance with the present invention including a 1:1 ratio of Stoller's BIO-FORGE® and Stoller's 2% chelated cobalt complex applied at a Pint/Acre compared to each individual component applied at a Pint/Acre.

DETAILED DESCRIPTION OF THE INVENTION

The present invention is an effective synergistic agricultural formula which comprises from 99.9 to 0.1 wt. % of at least one diacyl or diaryl urea and from 0.1 to 99.9 wt % of at least one metal complex. In one embodiment, the agricultural formula comprises from 20-0.1 wt. % of at least one diacyl or diaryl urea, preferably diformylurea, and from 0.1 to 20 wt % of at least one metal complex, preferably cobalt-metal complex. In one embodiment, the agricultural formula comprises from 10-0.1 wt. % of at least one diacyl or diaryl urea, preferably diformylurea, and from 0.1 to 10 wt % of at least one metal complex, preferably cobalt-metal complex. In one embodiment, the agricultural formula comprises from 5-0.1 wt. % of at least one diacyl or diaryl urea, preferably diformylurea, and from 0.1 to 5 wt % of at least one metal complex, preferably cobalt-metal. In one embodiment, the agricultural formula comprises from 2-0.1 wt. % of at least one diacyl or diaryl urea, preferably diformylurea, and from 0.1 to 2 wt % of at least one metal complex, preferably cobalt-metal. In one embodiment, the agricultural formula comprises from 2-0.5 wt. % of at least one diacyl or diaryl urea, preferably diformylurea, and from 0.5 to 2 wt % of at least one metal complex, preferably cobalt-metal. In one embodiment, the agricultural formula comprises 1 wt. % of at least one diacyl or diaryl urea, preferably diformylurea, and 1 wt % of at least one metal complex, preferably cobalt-metal.

In one embodiment of the present invention, the agricultural formula comprises a weight ratio of at least one diacyl urea, preferably diformylurea, at least one metal complex, preferably cobalt-metal, of 90:10-10:90. In another embodiment of the present invention, the agricultural formula comprises a weight ratio of at least one diacyl diaryl urea, preferably diformylurea, to at least one metal complex, preferably cobalt-metal, of 75:25-25:75. In another embodiment of the present invention, the agricultural formula comprises a weight ratio of at least one diacyl or diaryl urea, preferably diformylurea, to at least one metal complex, preferably cobalt-metal, of 60:40-40:60. In another embodiment of the present invention, the agricultural formula comprises a weight ratio of at least one diacyl diaryl urea, preferably diformylurea, to at least one metal complex, preferably cobalt-metal, of 52:48-48:50. In another embodiment of the present invention, the agricultural formula comprises a weight ratio of at least one diacyl diaryl urea, preferably diformylurea, to at least one metal complex, preferably cobalt-metal, of 1:1.

In one embodiment of the preferred embodiments recited herein, the only additional active ingredient in the agricultural formula is soluble potash ($K_2O$). Preferably, when soluble potash is added, the agricultural formula has a weight ratio of at least one diacyl or diaryl urea to at least one metal complex to soluble potash of 1:1:1. In one embodiment of the present invention, the agricultural formula includes the same amount of soluble potash as the at least one diacyl or diaryl urea and/or the at least one metal complex. In one embodiment, the agricultural formula includes 2-0.5 wt. % soluble potash, or 1 wt. % soluble potash.

The present invention is a benefit to crop system management and crop yield in the agriculture and horticultural industries. When applied during germination and establishment this results in an improvement in root architecture. When applied at flowering this results in the retention of flowers and increased fruit set. When applied during fruit sizing this results in a decrease in fruit drop and when applied post fruit sizing this results in a delay in ripening and extension of the cropping season. For example, N,N'-diformylurea when mixed with cobalt or other metals results in increased ethylene reduction for a prolonged length of time when compared to N,N'-diformylurea or cobalt and other metals alone.

While those skilled in the art will be able to prepare an aqueous solution of the synergistic agricultural formula at desired concentration depending on agricultural uses, it has been found that solutions containing from about 0.001-1.0 M of the active ingredients, i.e diacyl or diaryl urea and metal complex, are beneficial. Aqueous solutions containing from about 0.001-0.050 M are presently preferred. While these solutions may be applied at any rate desired by those of skill in the art, it has been found that aqueous solutions of the foregoing concentration provide good results when applied at the rate of about 15-750 ml. per 100 lbs of seed. Those skilled in the art would be aware that addition of a small quantity of oil and/or surfactant to the aqueous solution sprayed on the foliage will improve the adherence of the reaction product to the leaves and the uptake of the reaction product by the plant. Suitable oils include both saturated and unsaturated oils, alcohols, esters and other compounds having both hydrosphobic and hydrophilic functional groups. Exemplary oils comprise the vegetable oils and include sunflower oil and soybean oil. Exemplary biologically acceptable surfactants include the organic polyphosphates and ethoxylated nonophenols. Again, those skilled in the art can determine appropriate concentrations for each desired use. However, aqueous solutions having the foregoing concentrations are believed to be generally appropriate. These solutions should be applied at a rate sufficient to provide about 1-100 grams of reaction product per acre.

Diacyl or Diaryl Urea

As described in U.S. Pat. No. 6,040,273, the contents of which are expressly incorporated herein by reference, the preferred diacyl or diaryl urea of the present invention are the reaction products of a carboxylic acid and a urea having the formula

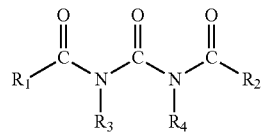

where $R_1$, $R_2$, $R_3$ and $R_4$ are the same or different and are selected from the group consisting of hydrogen, substituted and unsubstituted alkyl, allyl, vinyl and alkoxyl groups having from 1-6 carbon atoms, substituted and unsubstituted phenyl groups and the halides. Preferably, the reaction product of the present invention is N,N'-diformylurea or N,N'-diacetylurea. In one embodiment, these reaction products are prepared by reacting a carboxylic acid having the formula RCOOH where R is selected from the group consisting of hydrogen, substituted and unsubstituted alkyl, allyl, vinyl and alkoxyl groups having from 1-6 carbon atoms, substituted and unsubstituted phenyl groups and the halides. Exemplary acids include formic acid, acetic acid, propionic acid, butyric acid, valeric acid, caproic acid, heptanoic acid, and citric acid. Preferably R is selected from the group consisting of hydrogen and unsubstituted alkyl groups having from 1-3 carbon atoms. The presently most preferred acids are formic or acetic acid. These carboxylic acids are reacted with a substituted or unsubstituted urea having the formula $(NHR')_2$ CO where each R' is the same or different and is selected from the group consisting of hydrogen, substituted and unsubstituted alkyl groups having from 1-6 carbon atoms, substituted and unsubstituted alkoxyl groups having from 1-6 carbon atoms, substituted and unsubstituted phenyl groups and the halides. Unsubstituted urea is the presently most preferred reactant. In its most preferred embodiment, the present invention comprises the reaction product of urea and formic acid, i.e., N,N'-diformylurea, having the following formula

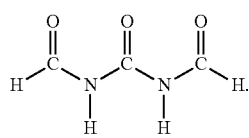

Furthermore, the agricultural formula may include diaryl ureas including, but not limited to, forchlorfenuron having the general formula:

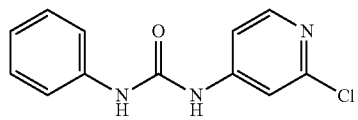

It has been found that the reaction will proceed throughout a wide range of temperatures, e.g., from about 10° C. to about 140° C., restricted only by the boiling points of the reactants and products. While heat may be added by any conventional means to speed the rate of these reactions, it has been found that the methods of the present invention may conveniently be performed in a temperature range from about 15° C. to about 40° C., preferably at room temperature, i.e., from about 20° C. to about 30° C. These reactions appear to be slightly exothermic. The reaction of formic acid and urea to form diformylurea proceeds to completion within 24 hours at room temperature. It is preferred that the reaction mixture be stirred until clear and then permitted to remain quiescent until crystals of the reaction product have formed. It is believed that the reactions proceed by the elimination of two water molecules. The reaction of urea and formic acid proceeds as follows: $H_2NCONH_2 + 2RCOOH \rightarrow RCONHCONHCOR + 2 H_2O$. In this reaction, formic acid reacts with one hydrogen on each of the urea nitrogens to produce N,N'-diformylurea. Accordingly, it is preferred that the reaction mixture comprise about 2 moles of carboxylic acid for each mole of urea.

A commercial embodiment of the at least one diacyl or diaryl urea included in the present agricultural formula includes BIO-FORGE® (manufactured by Stoller Enterprises, Inc. in Houston, Tex., USA). Also, see U.S. Pat. Nos. 6,448,440 and 6,710,085, the contents of which are incorporated herein by reference.

Metal Complex

The metal complex may be provided as an aqueous solution including a metal selected from the group consisting of the alkaline earth metals, the transition metals, boron and mixtures thereof. In one embodiment, the metals are selected from the group consisting of calcium, magnesium, zinc, copper, manganese, boron, iron, cobalt, molybdenum and mixtures thereof. A preferred metal is cobalt. When included, the metal may be present in an aqueous solution in a range from about 0.001 to about 10.0 percent-by-weight, preferably from about 0.001 to about 5.0 percent-by-weight, more preferably 1 to 3 percent-by-weight. In one embodiment of the present invention, STOLLER's 2% chelated cobalt complex is used including about 2 wt. % chelated cobalt in an aqueous solution (manufactured by Stoller Enterprises, Inc. in Houston, Tex., USA). In one embodiment of the present invention, the metal complexes include, but are not limited to, metal oxides, metal halides, metal sulfates, and/or chelated metal. In one embodiment of the present invention, the metal complex is metal sulfates, preferably cobalt sulfate.

The following Examples are used to illustrate one embodiment of the invention. However, it should be understood by one of ordinary skill in the art that other agricultural formulas may be modified from these preferred embodiments without departing from the scope of the present invention.

EXAMPLES

Tomato Fruit Retention

As those skilled in the art may attest, production of ethylene results in accelerated fruit drop. Stoller's BIO-FORGE®, a diformylurea formulation, mitigates the effect of stress ethylene by mitigating stress. Stoller's 2% chelated cobalt complex blocks the terminal enzyme in the synthesis of ethylene (ACCO). As seen in FIG. 1, a synergistic agricultural formula in accordance with the present invention including a 1:1 ratio of Stoller's BIO-FORGE® (which includes 2 wt. % diformylurea), and Stoller's 2% chelated cobalt complex (which includes 2 wt. % cobalt sulfate) applied at a Pint/Acre was found to reduce fruit drop significantly compared to each individual component applied at a Pint/Acre.

Although the present invention has been disclosed in terms of a preferred embodiment, it will be understood that numerous additional modifications and variations could be made thereto without departing from the scope of the invention as defined by the following claims:

We claim:
1. An aqueous solution of a synergistic agricultural formula consisting of:
  99.9 to 0.1 wt % of at least one diacyl urea,
  0.1 to 99.9 wt % of at least one metal complex including a metal selected from the group consisting of nickel, calcium, magnesium, zinc, copper, manganese, boron, iron, cobalt, molybdenum and mixtures thereof present in an aqueous solution,
  water,
  optional soluble potash,
  optional oil, and
  optional surfactant, wherein the metal complex with said metal selected from the group and the diacyl urea together provides synergy.

2. An aqueous solution of claim 1 consisting of 10 to 0.1 wt. % of said at least one diacyl urea and 0.1 to 10 wt. % of said at least one metal complex, water, optional soluble potash, optional oil, and optional surfactant.

3. The aqueous solution of claim 1 consisting of 5 to 0.1 wt. % of said at least one diacyl urea and 0.1 to 5 wt. % of said at least one metal complex, water, optional soluble potash, optional oil, and optional surfactant.

4. The aqueous solution of claim 1 consisting of 2 to 0.1 wt. % of said at least one diacyl urea and 0.1 to 2 wt % of said at least one metal complex, water, optional soluble potash, optional oil, and optional surfactant.

5. The aqueous solution of claim 1 consisting of 2 to 0.5 wt. % of said at least one diacyl urea and 0.5 to 2 wt. % of said at least one metal complex, water, optional soluble potash, optional oil, and optional surfactant.

6. The aqueous solution of claim 1 consisting of 1 wt. % of said at least one diacyl urea and 1 wt. % of said at least one metal complex, water, optional soluble potash, optional oil, and optional surfactant.

7. The aqueous solution of claim 1 wherein said at least one diacyl urea is diformylurea.

8. The aqueous solution of claim 4 wherein said at least one diacyl urea is diformylurea.

9. The aqueous solution of claim 6 wherein said at least one diacyl urea is diformylurea.

10. The aqueous solution of claim 1 wherein said at least one metal complex is a cobalt-metal complex.

11. The aqueous solution of claim 8 wherein said at least one metal complex is a cobalt-metal complex.

12. The aqueous solution of claim 10 wherein said at least one metal complex is a cobalt-metal complex.

13. The aqueous solution of claim 1 consisting of 99.9 to 0.1 wt % of said at least one diacyl urea, 0.1 to 99.9 wt. % of said at least one metal complex, water, 2-0.5 wt. % soluble potash, optional oil, and optional surfactant.

14. An aqueous solution of a synergistic agricultural formula consisting of:
  99.9 to 0.1 wt % of at least one diacyl urea,
  0.1 to 99.9 wt % of at least one metal complex including a metal selected from the group consisting of nickel, calcium, magnesium, zinc, copper, manganese, boron, iron, cobalt, molybdenum and mixtures thereof present in an aqueous solution,
  water,
  optional oil, and
  optional surfactant, wherein the metal complex with said metal selected from the group and the diacyl urea together provides synergy.

15. The aqueous solution of claim 14 wherein said at least one diacyl urea is diformylurea.

16. An aqueous solution of claim 1 consisting of 20 to 0.1 wt % of said at least one diacyl urea and 0.1 to 20 wt. % of at least one metal complex, water, optional soluble potash, optional oil, and optional surfactant.

* * * * *